United States Patent [19]

Sawamura et al.

[11] Patent Number: 4,985,358

[45] Date of Patent: Jan. 15, 1991

[54] METHOD FOR PROCESSING GLYCERIDE FATS AND OILS

[75] Inventors: Norio Sawamura, Hashimoto; Takaharu Matsuo, Sennan; Yukio Hashimoto, Kishiwada, all of Japan

[73] Assignee: Fuji Oil Company, Ltd., Osaka, Japan

[21] Appl. No.: 167,240

[22] Filed: Mar. 11, 1988

[51] Int. Cl.$^5$ .............. C12P 7/64; C11C 1/00; C11C 3/00; A23D 7/00
[52] U.S. Cl. .................. 435/134; 435/271; 536/115; 536/119; 536/124; 426/607; 426/601; 426/33; 260/410; 260/410.7; 260/410.9 R
[58] Field of Search ............. 435/134, 271; 536/115, 536/119, 124; 426/607, 601, 33; 260/410, 410.7, 410 R

[56] References Cited

U.S. PATENT DOCUMENTS

| | | | |
|---|---|---|---|
| 4,275,081 | 6/1981 | Coleman et al. | 435/134 |
| 4,377,686 | 3/1983 | Feuge et al. | 536/119 |
| 4,705,692 | 11/1987 | Tanaka et al. | 426/607 |
| 4,874,699 | 10/1989 | Maruzeni et al. | 435/134 |

Primary Examiner—Herbert J. Lilling
Assistant Examiner—Pamela S. Webber
Attorney, Agent, or Firm—Wenderoth, Lind & Ponack

[57] ABSTRACT

A method for processing glyceride fats and oils which comprises the steps of subjecting a mixture of a glyceride fat or oil and a monohydric alcohol fatty acid ester to an enzymatic ester interchange reaction; distilling the reaction mixture of the ester interchange reaction to separate a distillate from a processed glyceride fat or oil to recover the latter; subjecting the distillate to an esterification reaction to lower its acid value; and recycling the distillate for use as a starting material for the ester interchange reaction.

6 Claims, No Drawings

METHOD FOR PROCESSING GLYCERIDE FATS AND OILS

FIELD OF THE INVENTION

The present invention relates to a method for processing glyceride fats and oils. More particularly, it relates to a method for an enzymatic ester interchange reaction of glyceride fats and oils in a recycle system.

BACKGROUND OF THE INVENTION

The present inventors have already proposed a method for processing glyceride fats and oils wherein glyceride fats and oils are subjected to an ester interchange reaction in a recycle system (Japanese Patent Kokai No. 56-163196 and U.S. Pat.No. 4,420,560). This method is suitable for the production of a hard butter and, in this method, a mixture (a) of a glyceride fat or oil to be processed (b) and a fatty acid ester or fatty acid (c) is subjected to a selective ester interchange reaction, and a fatty acid ester or fatty acid (d) and a desired processed glyceride (e) present in the reaction mixture (f) are separated therefrom followed by preparing the hard butter from the glyceride (e). This method is characterized by recycling the material (d) as a part of the mixture (a). The material (d) includes an unreacted fatty acid ester or fatty acid (c), if any, and that formed by the ester interchange reaction.

However, in the above method, when a fatty acid, especially a saturated fatty acid, is used as the material (c), there is a restriction that it is necessary to use a solvent in the ester interchange reaction. In addition, there is a problem that non-selective ester interchange (isomerization) takes place during distillation for separating the materials (d) from (e) in the reaction mixture (f), which impairs the advantage brought by the selective ester interchange.

In the case that a monohydric alcohol fatty acid ester is used as the material (c) in the above method and a fatty acid ester as the material (d) is recycled repeatedly, isomerization still takes place during the distillation step for separating the material (d) from the material (e), which results in a slight deterioration of a product. Further, when the fatty acid ester (d) is recycled repeatedly, there are problems that crystals may be separated out in the mixture (a), resulting in clogging when an immobilized enzyme is used, and reactivity is lowered.

Therefore, a solution to these problems has been requested.

OBJECTS OF THE INVENTION

The present inventors have newly found that the problems in the use of a monohydric alcohol fatty acid ester as the material (c) would be caused by slight decomposition of a monohydric alcohol fatty acid ester and a glyceride fat or oil upon recycling the fatty acid ester (d) repeatedly, and it is of importance to keep the acid value of the material (c) low in order to solve the problems.

The main object of the present invention is to provide an improved method for processing glyceride fats and oils wherein the above problems of a conventional method are solved.

This object as well as other objects and advantages of the present invention will become apparent to those skilled in the art from the following description.

SUMMARY OF THE INVENTION

According to the present invention, there is provided a method for processing glyceride fats and oils which comprises the steps of:

subjecting a mixture of a glyceride fat or oil and a monohydric alcohol fatty acid ester to an enzymatic ester interchange reaction;

distilling the reaction mixture of the ester interchange reaction to separate a distillate from a processed glyceride fat or oil to recover the latter;

subjecting the distillate to an esterification reaction to lower its acid value;

and recycling the distillate for use as a starting material for the ester interchange reaction.

Preferably, in the method of the present invention, the distillation is carried out by simple distillation followed by steam distillation, and only a fraction distilled off by steam distillation is subjected to the esterification reaction.

DETAILED DESCRIPTION OF THE INVENTION

The following explanation is principally directed to the method wherein the objective processed glyceride fat or oil is a hard butter mainly composed of triglycerides containing saturated fatty acid residues at 1- and 3-positions and unsaturated fatty acid residues at 2-position thereof (SUS type fat). However, any additional modification can be added according to a particular type of the objective fats and oils, and such modifications are also within the scope of the present invention.

In order to obtain the above hard butter, preferably, the glyceride fat or oil used as a starting material is that containing fatty acid residues which are rich in oleic acid residue at 2-position thereof. More preferably, 70% or more of the fatty acids bonded at 2-position is oleic acid. Examples of the glyceride fat or oil starting material include sunflower oil, oleic safflower oil, olive oil, camelia oil, PMF (palm oil mid-fraction), shea olein, sal olein and cotton seed olein.

The monohydric alcohol fatty acid ester is a source for introducing fatty acid residues into the glyceride fat or oil starting material to process the fat or oil and, usually, an ester of palmitic acid or stearic acid with $C_{1-4}$ lower monohydric alcohol is preferred. Examples of the monohydric alcohol fatty acid ester include methyl stearate, ethyl stearate, propyl stearate, methyl palmitate, ethyl palmitate and propyl palmitate.

The glyceride fat or oil and the monohydric alcohol fatty acid ester is subjected to an enzymatic ester interchange reaction. The enzymatic ester interchange reaction can be carried out according to a known method under known conditions. Preferably, the water content of the reaction system is adjusted to 0.18% by weight or lower (including water derived from an enzyme and a solvent used) based on the substrate from the beginning of the reaction, or by drying during the reaction. Further, it is preferred to use an enzyme having such selectivity that the ester interchange reaction takes place predominantly at 1- and 3-positions but hardly at 2-position. The temperature of the ester interchange reaction may vary depending upon the heat resistance of the enzyme. However, usually, a temperature not lower than 30° C. is preferred.

In the method of the present invention, the reaction mixture of the ester interchange reaction is distilled to separate a distillate from the objective processed glyceride fat or oil to recover the fat or oil. And, the acid value (hereinafter abbreviated as AV) of the distillate is lowered by subjecting it to an esterification reaction. Then, the distillate thus esterified to lower its AV is recycled for use as a starting material of the ester interchange reaction. Thereby, isomerization during the distillation step can be prevented and, when an immobilized enzyme is used, clogging and lowering of reactivity can be also prevented.

Distillation can be carried out by simple distillation (by simply raising a temperature under reduced pressure, e.g., up to 250° C. under a pressure of 1 to 5 mmHg). However, as described above, preferably, steam distillation is carried out after simple distillation. That is, in simple distillation, it is difficult to sufficiently remove fatty acids and fatty acid esters from the processed glyceride fat or oil unless employing considerably high vacuum and, thereby, the yield is considerably decreased. On the other hand, by employing simple distillation and then steam distillation (e.g., 200° to 250° C. under a pressure of 1 to 5 mmHg), fatty acids and fatty acid esters can be sufficiently removed from the processed glyceride fat or oil without decrease in yield. Further, since AV of a fraction distilled off during the steam distillation step is higher than that of a fraction distilled off during the simple distillation step, the desired result can be attained by esterification of the former fraction alone, which results in good efficiency.

The remaining desired processed glyceride fat or oil can be recovered according a known method and can be used for the production of a hard butter and the like according to a known method.

The esterification reaction can be carried out according to a known method. For example, an excess of monohydric alcohol is added to the distillate and the mixture is heated in the presence of an acid catalyst (e.g., sulfuric acid, p-toluenesulfonic acid, etc.). If necessary, a known decoloring step can be added. As described above, there is no need to subject the whole distillate to esterification and therefore there is no need to esterify completely. The essential thing is to keep the AV of the mixture of fatty acids and fatty acid esters recycled into the mixture of the starting materials for the ester interchange reaction below a certain value as described hereinafter.

The desired AV of a mixture of fatty acids and fatty acid esters contained in a mixture of the starting materials of the ester interchange reaction may vary depending upon the temperature of the ester interchange reaction and the mixing ratio of the glyceride fat or oil starting material and the mixture of fatty acids and fatty acid esters, and can not be defined uniformly. However, in general, when the reaction temperature is higher, or the mixing ratio of the mixture of fatty acids and fatty acid esters to the glyceride fat or oil is lower, a higher AV is acceptable. For example, when the reaction temperature is 40° C. and the amount of the mixture of fatty acids and fatty acid esters is the same as that of the glyceride fat or oil starting material, in general, the AV should be not more than 15, preferably, not more than 8. When the AV is higher than 15, crystals may be precipitated in the mixture of the starting materials of the ester interchange reaction, which results in clogging of an immobilized enzyme bed or decrease in reactivity unless a solvent is used. When the AV becomes not more than 8, isomerization during distillation hardly occurs, which results in a best quality or a best yield of the triglyceride fat or oil obtained from the reaction mixture of the ester interchange reaction.

Preferably, the above distillate may be hydrogenated before or after esterification, and then recycled for use as a starting material of the ester interchange reaction. When the degree of hydrogenation is higher, the yield of the desired hard butter is higher with minimum deterioration of the quality thereof, or the quality of the desired hard butter is more improved without decrease in the yield.

The desired triglyceride fat or oil recovered from the reaction mixture can be used as the desired hard butter as it is, or after fractionation thereof to remove its high melting point and/or low melting point fractions. This fractionation to remove the high melting point and/or low melting point fractions can be carried out according to a method known in the art to produce a hard butter. The whole of the glyceride fat or oils recovered from the reaction mixture or the low melting point fraction can be recycled for use as a part of the starting material of the ester interchange reaction, thereby an excellent hard butter can be obtained in a good reactivity and good yield, even when a triglyceride fat or oil having a saturation degree extremely lower than that of the objective fat or oil is used as the starting material.

If necessary, the above low melting point fraction or the starting triglyceride fat or oil of the ester interchange reaction can be treated with an enzyme having a specificity for a partial glyceride to selectively hydrolyze the partial glyceride. Such a treatment can lower the diglyceride content of the starting material of the ester interchange reaction. Thereby, the quality of the hard butter obtained from the ester interchange reaction can be improved. Or, since the restriction of an amount of diglycerides which restricts the production of a hard butter having a certain quality level can be moderated, it is possible to slightly increase in the water content in the system of the ester interchange reaction to improve reactivity. Further, deacidification of free fatty acids formed by this specific hydrolysis of the partially glyceride can be eliminated because the AV of the system can be controlled by the above esterification, which advantageously results in improvement in yield and simplification of steps.

The reaction of the partial glyceride specific enzyme can be carried out in the presence of a small amount of water. This amount of water in the enzymatic reaction system is not less than 0.2%, preferably not less than 1%, more preferably 5 to 15% by weight of water based on the substrate glyceride fat or oil. When the water content is less than 0.2% by weight, the diglyceride component is hardly hydrolyzed. On the other hands, when the amount of the enzyme is too high, it is uneconomical. If necessary, the enzyme can be immobilized to facilitate its recovery and continuous reaction. Usually, the reaction time of 10 minutes to 24 hours is sufficient and the appropriate reaction time can be chosen according to the concentration of the enzyme. When the reaction is carried out with a larger amount of the enzyme for a longer period of time, it is necessary to take care of decomposition of the triglyceride fat or oil that the triglyceride fat or oil because it is liable to be decomposed under such conditions. Thus, preferably, the reaction should be completed within 4 hours. The reaction temperature is generally in the range of 20° to 85° C. and can be chosen according to a particular enzyme used.

The following Examples further illustrate the present invention in detail but are not to be construed to limit the scope thereof. All "parts" and "%'s" are by weight unless otherwise stated.

Example 1

A commercially available lipase of *Rhizopus delemar* (1 part) was mixed with diatomaceous earth (2 parts) and to the mixture was sprayed a suitable amount of cold water with stirring to granulate the mixture. The granules obtained were gradually dried at 15° C. under reduced pressure to give a diatomaceous earth-enzyme preparation having a water content of 1.5%. Separately, refined safflower oil (high-oleic) (100 parts) and methyl stearate (100 parts) were heated and dried under reduced pressure to prepare a reaction substrate (water content: 0.02%; AV of the starting material: 10). To the substrate was added the above diatomaceous earth enzyme preparation (10 parts) and the resulting mixture was stirred at 45° C. in a closed system for 3 days followed by recovering the resulting product. The reaction product was subjected to simple distillation at 220° C. at 3 mmHg and then to steam distillation at 230° C. at 3 mmHg wherein the ratio of the fractions distilled off during the two steps was adjusted to about 95:5. The latter fraction was esterified with a small amount of stearic acid (in such an amount that the amount after hardening became 100 parts) and an excess of ethanol using sulfuric acid catalyst and, after the AV thereof was adjusted to 3, the resultant was combined with the former fraction, the mixture was completely hardened by hydrogenation and recycled to use as the starting material of the ester interchange reaction.

The remaining glyceride fat or oil after distillation was fractionated into solid and liquid phases. The solid phase was used for preparation of a hard butter. To the liquid phase was added a high-oleic safflower oil (100 parts) and the mixture was also recycled for use as the starting material of the ester interchange reaction.

As a control, the above procedure for recycling the distillate was repeated except that the esterification of the distillate was not effected.

After 8 cycles, the AV of the above hardened product of the present example was 10, while that of the control was 35, and reactivity of the ester interchange reaction (reactivity per unit time) after 8 cycles of the control was 75% of that of the present example.

$T_{max}$ of a cooling curve (according to Jensen's method) of the hard butter obtained (fractionation yield: 34%) was 28.2° C., while that of the control hard butter (yield, 31%) was 27.3° C.

Example 2

The same recycle system as Example 1 was repeated except that the starting glyceride fat or oil and the fatty acid ester were reacted by passing through a column filled with an enzyme at 40° C. Likewise, as a control, the same procedure was carried out except that no esterification was effected.

In the control, crystals of raw substrate were deposited out in the enzyme column after 20 cycles to become clogged, preventing smooth passage. On the other hand, in the present example, no deposition of crystals was observed and the substrate passed through the column without any difficulty.

Example 3

The same recycle system as Example 1 was repeated except that the partial glyceride of the liquid phase obtained by the fractionation of the remaining glyceride fat or oil after distillation was treated by selective hydrolysis, dehydrated and mixed with high oleic safflower oil without deacidification. The resultant (100 parts) was recycled to use as the substrate. A control was carried out without esterification.

For selective hydrolysis of the partial glyceride, an enzyme obtained from a strain of Penicillum (manufactured and sold under the trade name of "Lipase G" by Amano Seiyaku K.K., Japan) (strength per 1 mg of enzyme: 0.42) was used as the partial glyceride specific enzyme. The Enzyme was used in an amount of 0.01% based on the substrate and the initial water content in the system was adjusted to 10%.

In the present example, deacidification was not required for recycling. However, in the control, AV of the completely hardened product was 31 after 6 cycles, and the reactivity was 85% of that of the present example as the same recycling stage.

What is claimed is:

1. A process for processing glyceride fats and oils which comprises the steps of:
    subjecting a mixture of a glyceride fat or oil and a monohydric alcohol fatty acid ester to an enzymatic ester interchange reaction;
    distilling the reaction mixture of the ester interchange reaction to separate a distillate from a processed glyceride fat or oil to recover the latter;
    subjecting the distillate to an esterification reaction to lower its acid value;
    and recycling the distillate for use as a starting material for the ester interchange reaction.

2. A process according to claim 1, wherein the distillation is carried out by simple distillation followed by steam distillation, and only a fraction distilled off by steam distillation is subjected to the esterification reaction.

3. A process according to claim 1, wherein the glyceride fat or oil to be processed is that containing fatty acid residues which is rich in oleic acid residues at 2- 0 -position thereof.

4. A process according to claim 3, wherein 70% or more of the fatty acids bonded at 2-position of the glyceride fat or oil to be processed is oleic acid.

5. A process according to claim 1, wherein the monohydric fatty acid ester is an ester of palmitic acid or stearic acid.

6. A process according to claim 5, wherein the ester is a $C_{1-4}$ lower monohydric alcohol ester.

* * * * *